United States Patent [19]

Keyes

[11] 4,206,286

[45] Jun. 3, 1980

[54] IMMOBILIZATION OF PROTEINS ON INORGANIC SUPPORTS

[75] Inventor: Melvin H. Keyes, Sylvania, Ohio

[73] Assignee: Technicon Instruments Corporation, Tarrytown, N.Y.

[21] Appl. No.: 850,890

[22] Filed: Nov. 14, 1977

[51] Int. Cl.² .................. C07G 7/00; C07G 7/02
[52] U.S. Cl. ............................. 435/176; 435/190
[58] Field of Search .............. 195/63, 68, DIG. 4; 260/112 R; 435/176, 190

[56] References Cited

U.S. PATENT DOCUMENTS

| | | | |
|---|---|---|---|
| 3,519,538 | 7/1970 | Messing et al. | 195/63 |
| 3,796,634 | 3/1974 | Haynes et al. | 195/68 X |
| 3,804,719 | 4/1974 | Messing | 195/63 X |
| 3,850,751 | 11/1974 | Messing | 195/63 |
| 3,873,426 | 3/1975 | Katchalski et al. | 195/63 |
| 3,930,951 | 1/1976 | Messing | 195/63 |
| 3,969,287 | 7/1976 | Jaworek et al. | 195/68 X |
| 3,982,997 | 9/1976 | Eaton et al. | 195/63 X |
| 4,004,979 | 1/1977 | Arrameas et al. | 195/68 |

OTHER PUBLICATIONS

Martensson, K., Preparation of an Immobilized Two-Enzyme System, B-Amylase-Pullulanase to an Acrylic Copolymer for the Conversion of Starch to Maltose, Biotechnol, and Bioeng. vol. XVI, 1974 (pp. 567–577).

*Primary Examiner*—David M. Naff
*Attorney, Agent, or Firm*—S. P. Tedesco

[57] ABSTRACT

A method of producing an immobilized protein composite, i.e. enzymes such as glucose oxidase, on an alumina support, comprising modifying some of the free functional groups of the protein such as amino groups, by reaction with an acid or anhydride, depositing the modified protein on a porous inorganic support at controlled pH and temperature, and cross-linking remaining free functional groups of the protein with adjacent deposited protein functional groups to form interprotein peptide bonds. The resultant composite has long-term continuous use.

17 Claims, No Drawings

4,206,286

IMMOBILIZATION OF PROTEINS ON INORGANIC SUPPORTS

BACKGROUND OF THE INVENTION

1. Field of the Invention

This invention relates to catalytically active enzymes and more particularly to immobilized enzymes deposited on inorganic materials. Enzymes usually have high molecular weights, can catalyze numerous specific chemical reactions, and techniques have been developed to increase their efficiency in use. These techniques were developed because the enzymes are generally water soluble and for this reason when used in solution, they can only be used batch-wise, since it is difficult to remove them from the reaction medium. The techniques developed were directed to the immobilization or fixing of the enzymes on substantially water insoluble supports without loss of activity so that the enzymes could be used repeatedly.

2. Description of the Prior Art

In the past, enzymes have been fixed or immobilized on both organic and inorganic supports. Enzymes can be immobilized on particles of various metal oxides so that the enzyme is bound or deposited on the surface of the oxide and is supported thereat to catalyze a specific reaction as shown for example in U.S. Pat. No. 3,850,751. This type of immobilization, while satisfactory, has the disadvantage that the enzyme will also desorb or release itself from the surface of the support over a period of time. The activity of the composite is thereby lowered over the long term, and the sample is contaminated with active enzyme which continues to react with the substrate after the sample has been removed from the reaction chamber of analysis. Accordingly, data for a given sample or batch may be obtained which may not be truly representative of the nature of the sample.

Many techniques have been attempted to lessen the rate at which enzymes desorb from a support structure. In U.S. Pat. No. 3,873,426, the enzyme and an organic dye, typically a halotriazine dye, are adsorbed onto alumina below pH 7. This code-position proposes to increase the affinity of the enzyme for the support. In such techniques, the enzyme and the added species, in this example the dye, can desorb into the test sample at some finite rate. Accordingly, another possible contaminant can be introduced in the test sample which gives false results when the sample is examined spectrophotometrically or electro-chemically.

U.S. Pat. No. 3,982,997 discloses the use of mixed metal oxides to immobilize enzymes and increase deposition of the enzyme and stability of the composite. While the technique does exhibit an increased initial activity of the enzyme, it does not bind the enzyme to the support which approximates an ideal strength of binding.

Many techniques have been utilized to covalently link an enzyme to the support to circumvent the desorption problems encountered in techniques as discussed above. These techniques of covalent bonding have generally used a coupling agent which bonds to the support by one reactive group and bonds to the enzyme by another reactive group. These groups have generally been reactive species such as diazos, silanes, and the like. For examples of these coupling agents reference is made to U.S. Pat. No. 3,930,951, and U.S. Pat. No. 3,519,538.

Many of these immobilization techniques have been used in large scale operation but have not been completely satisfactory. This is due to the expense in production of the composite, the lack of long-term stability of the composite, certain difficulties involved in purifying the coupling agents from the composite after its production, and in the gradual desorption of these additives into delicate samples or electrode systems used to monitor the product levels in the reactor.

SUMMARY OF THE INVENTION

An object of the present invention is to simplify and reduce the cost of enzyme immobilization.

Another object of the present invention is to form an enzyme-support composite which is easily removed from the reaction media and has a long catalytic lifetime.

A further object of the present invention is to form an enzyme-support composite which is relatively free from contaminating materials which were used in the synthesis of the composite.

The method according to the present invention produces an immobilized enzymatic protein composite and briefly comprises the steps of selecting an enzyme having free amino-functional and carboxyl-functional groups, modifying the enzyme by reacting some of the functional groups on the enzyme with a modifying agent to facilitate the deposition of the enzyme on the support to produce a modified enzyme, depositing the modified enzyme on a water insoluble, inorganic support, wherein said deposition is facilitated by the modification of the functional groups, and reacting the adjacent enzymes to form cross-linking peptide bonds therebetween.

DETAILED DESCRIPTION OF THE INVENTION

The present invention is concerned with the chemical and physical properties of the enzymes, and the properties of metal oxides in aqueous solution. In particular, a new method was found to immobilize most enzymes on an inorganic support by modifying the enzyme from its normal solution state to a second state. In the second state, the modified enzyme has a relatively higher affinity for binding to a positively charged surface, such as alumina, than in its normal enzyme solution state wherein it will deposit or "bind" with a support with a relatively lower affinity. In addition, a new method was found for cross-linking the deposited enzymes on the support so as to yield limited "polymerization" of the support bound enzymes without resorting to the expedient of covalently bonding the enzyme to a coupling molecule (typically a diazo or silane species) and then reacting the coupling molecule with a reactive group on the support. Importantly, since the new method employs groups contained by the enzyme in the cross-linking process, a bridging group is not needed to cross-link the proteins. Although it has been heretofore considered necessary to use a bifunctional molecular chain, usually containing four carbon atoms or more, to link the enzymes to each other, once they are deposited on the support, it has been demonstrated by the present invention that this is not necessary.

The method of preparing the desired enzyme-support composite according to the present invention is as follows. In a preferred embodiment of the composite, an inorganic support is selected which contains pores on the order of about 0.1 micron over a large proportion of its surface area. These pore sizes are sufficient to allow the infiltration of enzymes of geometry and size similar to that of, for example, glucose oxidase into the cavities of the pores. Thus, an enzyme can be deposited on the exterior surface of the particles and also on a relatively large interior surface area of the walls of the interior surfaces of the pores. The inorganic support can be a metal oxide and alumina is preferred since alumina is fairly inexpensive and has good durability, mechanical strength, and stability on exposure for long periods to acidic and basic solutions. The preferred support, alumina, is sieved through an 80 mesh sieve to remove particles which are too small to be useful, and foreign particulates which are contaminating the support. The alumina is then washed with distilled, deionized water until clarified wash water is achieved. After the wash, the alumina is drained and placed in a 6 M HCl solution for a period of time, generally on the order of 1 to 2 hours at room temperature. The alumina is suction dried, then washed again and stored wet. This procedure produces a particle of alumina, or other metal oxide suitable for this procedure as a support which shows a net positive charge on the surface up to around pH 9.

Alumina has a net positive charge in aqueous solution to around pH 9, and will substantially hinder the deposition of many enzymes from aqueous solution, since a very large class of proteins have a net positive charge in the same pH range as is the alumina. When attempting to noncovalently bind or deposit the enzyme to the alumina at these pH's, electrostatic repulsion is encountered which is typical of two positive bodies being placed in proximity. This phenomenon may account for some of the difficulties traditionally experienced in the noncovalent attachment of enzymes to metal oxide supports.

To convert this net positive surface from a disadvantage to an advantage, a normal enzyme is treated as follows to modify its structure so as to increase its affinity for the support. The modified enzyme will bind with the support much more strongly than normal enzymes subjected to complicated methods to precondition or to derivitize the support.

According to the present invention, an enzyme for example having free amino-functional groups, is reacted in solution, at around pH 7.5 with a modifying agent which preferably is an organic acid or anhydride, e.g. succinic anhydride, succinic acid, malic acid or anhydride, and glutaric anhydride. The acid or anhydride reacts with and modifies the enzyme wherein the modified enzyme will bind more tightly to the support material.

The above method has converted an enzyme which is thought to show a net positive charge at this solution state to a modified enzyme which will, at the proper pH, spontaneously and strongly bind with the positive surface of the inorganic support. The modified enzyme is mixed with the support and the pH of the mixture is changed to one in which the enzyme binds most tightly to the support. A cross-linking agent is added to the mixture which will catalyze or assist in the reaction of a free amino group, (i.e. on an enzyme which was not reacted with a molecule of modifying agent) one with a free carboxyl group from another enzyme which is situated adjacent the amino donating enzyme on the support to form an amide, i.e. a peptide bond.

Table I shows a long-term stability of the deposited enzyme composite of the present invention. The table shows the effect of using modifying agent on the activity and long-term stability of the composite. The table shows assay results as percent conversion of substrate to product, after extended periods of use. The composite samples were packed into cylindrical cartridges of approximately 0.5 cc volume through which the samples were passed in a flowing buffer stream.

The batch indicates a particular sample of glucose oxidase-alumina composite which was used in the test. The enzyme glucose oxidase generates hydrogen peroxide and gluconic acid from glucose, water, and oxygen. To measure the percent of conversion a composite batch was loaded into a flow-through reactor and a number of discrete samples were passed through the column. The hydrogen peroxide generated was detected polarographically. The column "No. of Runs" indicates the number of samples which had flowed through the column when the measurement was taken. For example, in batch number one, after 799 samples were passed through the composite packed column, the 800th sample was standardized to a predetermined glucose concentration. The sample was passed through the column and the resultant hydrogen peroxide was measured. The equivalent glucose value was calculated and the percent conversion of glucose to gluconic acid was determined.

TABLE I

| Batch | "Retention of Conversion Activity After Extended Composite Use" | | |
|---|---|---|---|
| | | % Conversion | No. of Runs |
| 1 | | 100 | 800 |
| 2 | greater than | 95 | 1800 |
| 3 | | 90 | 1000 |
| 4 | | 90 | 2000 |

The composites used in Table I were typically prepared by the following procedure: Thirty gm of $-60+70$ mesh porous alumina having 0.1 micron diameter pore size is sieved through an 80 mesh screen for five minutes. After the alumina is washed with one liter of distilled, deionized water, it is placed under 200 ml of 6 N HCl for 1.0 hour.

Sufficient glucose oxidase (Sigma Type II) is dissolved in 30 ml of distilled water to give an absorbance of 1.16 at 450 nm and the pH adjusted with 0.1 N HCl or NaOH to pH 7.5. Ten mg of succinic anhydride dissolved in 1 ml of acetone is added to the glucose oxidase solution in 0.1 ml aliquots. One aliquot is added every ten minutes and the solution is stirred for 20 minutes after complete addition. After the alumina is washed of HCl solution and deaerated in the presence of 200 ml of distilled water, the wet alumina is mixed with the succinic anhydride treated glucose oxidase solution. The pH is adjusted to 4.2 and 0.1 g of 1-ethyl-3-(3-dimethylaminopropyl)-carbodiimide HCl (EDC) is added. This combination of material is allowed to react overnight (16–18 hours) at 0°–5° C. with gentle shaking. During this reaction time, a solution of 0.4 g EDC in 30 ml distilled water is added at the rate of about 0.1 ml/min. The next day, the pH is 5.7, and the absorbance 0.221 at 450 nm. The alumina-glucose oxidase composite is washed with 2 l of 0.2 M $(NH_4)_2SO_4$ (enzyme grade-Schwartz Mann) followed by 4 l of distilled, deionized water. The composite is stored in distilled water and the initial activity was 57.9 U/ml of $Al_2O_3$, which corresponds to a loading fraction of about 2 mg/ml.

Table II shows the effect of modifying agent on the activity of the composite. As shown by the table, when modified protein is deposited, there is consistently higher activity than when non-modified enzyme is deposited, under substantially the same circumstances. The enzyme was deposited in the examples of non-modified enzyme according to the procedure of sieving 30 grams of alumina through an 80 mesh screen for 5 minutes. The alumina is washed until clear with distilled water, then allowed to stand under two hundred ml of six molar hydrochloric acid for one hour. About thirty ml of a glucose oxidase solution is adjusted to pH 7.5. The alumina is washed until clear with distilled water, and suction deaerated. The alumina is added to the glucose oxidase solution and the material is adjusted to pH 4.2. About 0.1 grams of EDC is added and dissolved. Next, 0.4 grams of EDC in 30 mls of water is added to the composite at a rate of about 0.1 ml/min. The composite is allowed to react overnight (16–18 hours) at about 0°–5° C. with gentle shaking. The next day the composite is washed with 2 liters of 0.2 M $(NH_4)_2SO_4$ (enzyme grade-Schwartz Mann), followed by 4 liters of distilled water. The batch is stored under distilled water.

Table II compares three batches, all of which were formed as described above. The enzyme concentration column defines the approximate concentration of enzyme in aqueous solution when the alumina of the composite was added. The batch pairs were as equally matched as possible. The composite samples were packed into a flow-through system as in the procedure of Table I, and a standard glucose sample was flowed therethrough. The amount of glucose converted to gluconic acid was calculated and a percent increase was calculated.

TABLE II

| Batch | Enzyme Concentration in $M \times 10^{-5}$ | Relative Activity | % Increase |
|---|---|---|---|
| 1 With modifying agent | 0.88 | 30 | 36 |
| Without modifying agent | 0.88 | 22 | |
| 2 With modifying agent | 0.28 | 22 | 22 |
| Without modifying agent | 0.28 | 18 | |
| 3 With modifyng agent | 0.66 | 36 | 44 |
| Without modifying agent | 0.70 | 25 | |

The cross-linking reaction is typically catalyzed by a carbodiimide, e.g. 1-ethyl-3-(3-dimethylaminopropyl)-carbodiimide HCl, or 1-cyclohexyl-3-(2-murpholine-thyl)-carbodiimide metho-p-toluene sulfonate. The carbodiimide is believed to react with the enzyme carboxyl to form an unstable intermediate which then reacts with the adjacent proteins' amide group to form the corresponding peptide bond and split out the ketone corresponding to the original carbodiimide. In this manner, a direct enzyme-enzyme link is formed to more or less "polymerize" the enzyme on the surface of the support. The cross-linking method allows for the ease of removal of all extraneous by-products and reactants in a solution which may lower the effectiveness or purity of the resultant composite. The term catalyze here is not to be construed as indicating that the original diimide is returned to solution after the formation of the peptide bond in its pre-reaction structure. The term is used only to indicate that the diimide initiates and facilitates the peptide bond synthesis. If the diimide were a self-renewing species, i.e. a "true" catalyst, it would be needed only in small amounts. The diimide should be added at the beginning of the reaction and in aliquots during the polymerization, because it is converted in the reaction and also because the diimides are easily degraded in water and therefore must be replenished during the course of the reaction. Typically a unit amount of diimide is added to start the reaction and the mixture is shaken for about 16–18 hours in the cold with continuous addition of aliquots of a second diimide solution.

Upon the completion of the "polymerization" the composite is washed with a buffer, then deionized water, and stored. This procedure gives an enzyme-support composite which is extremely stable over substantially all the pH and temperature ranges in which enzymes like glucose oxidase are usually and normally active. These composites, when packed in a flow-through columns, have been found to be stable and give linear catalytic activity results for up to about 2,000 reaction cycles. This indicates a substantial improvement over the prior art methods and products, and is of great practical importance for continuous flow-through type reactors or clinical instruments which test hundreds of samples per week.

The method of the invention has been found to be amenable to a wide variety of enzymes and is particularly well suited to the immobilization of protein in general. The following examples illustrate the preparation of support bound glucose oxidase (hereinafter G.O.) enzyme for use in a composite according to the present invention. It is understood that the present method applies equally well to a large class of proteins and enzymes, the enzyme G.O. being merely a representative embodiment. The enzyme G.O. has been successfully deposited from a number of sources in accordance with this invention, particularly that enzyme purchased from Sigma Chemical as Sigma Type II G.O.; from Worthington Chemical Co. as Worthington Grade G.O.; from Miles Labs, Inc., as pure G.O. (i.e. nearly catalase free) and from P-L Biochemical Company as P-L G.O. No. 197-7. Similarly, the alumina, buffer components, acids, anhydrides and inorganic acids are standard enzyme grades available commercially.

EXAMPLE I

PREPARATION OF G.O. ON HEXYL HYDROPHOBIC GEL

Eight g of Sigma Type II G.O. is dissolved in 10 ml of distilled water and is dialyzed overnight against 2 mM $PO_4$, pH 7.0. The resulting solution (approximately 50 ml) is applied to a column of n-hexyl hydrophobic gel (Miles Laboratories, Inc.) (1 cm $\times$ 30 cm). The column is eluted with 2 mM $PO_4$ buffer, pH 7.0 and any protein material eluted is discarded. Next, the column is eluted with 0.05 M $PO_4$ buffer, pH 7.0 and the protein eluted contained G.O. which is used for enzyme immobilization. The separation procedure set forth aids in the separation of any catalase which is present and which could contaminate the purified G.O. Although the presence of catalase will not diminish the activity of the G.O., it could produce variations in the desired results where the immobilization of the G.O. also produces a catalase substrate.

EXAMPLE 2

IMMOBILIZED G.O.

30 g of $-60+70$ mesh (United States Standard Sieve) porous alumina having 0.1 micron diameter pore size is sieved through an 80 mesh screen for five minutes. After the alumina is washed with one liter of distilled, deionized water, it is placed under 200 ml of 6 M HCl for 1.0 hour. Sufficient G.O. (Sigma Type II) is dissolved in 30 ml of distilled water to give an absorbance of 1.16 at 450 nm and the pH adjusted with 0.1 ml aliquots. One aliquot is added every ten minutes and the solution is stirred for 20 minutes after complete addition. After the alumina is washed of HCl solution and deareated in the presence of 200 ml of distilled water, the wet alumina is mixed with the succinic anhydride treated, G.O. solution. The pH is adjusted to 4.2 and 0.1 mg of 1-ethyl-3-(3-dimethylaminopropyl)-carbodiimide HCl (EDC) is added. This combination of material is allowed to react overnight (16-18 hours) at $0°-5°$ C. with gentle shaking. During this reaction time, a solution of 0.4 mg EDC in 30 ml distilled water is added at the rate of about 0.1 ml/min. The next day, the pH is 5.7 and the absorbance 0.221 at 450 nm. The alumina-G.O. composite is washed with 4 l of 0.2 M $(NH_4)_2SO_4$ (enzyme grade-Schwartz Mann) followed by 4 l of distilled, deionized water. The composite is stored in distilled water and the initial activity was 57.7 U/ml of alumina.

EXAMPLE 3

IMMOBILIZED G.O.

20 mg of $-40+50$ mesh (United States Standard Sieve) porous alumina having about 0.1 micron diameter pores are sieved through 80 mesh screen for five minutes. After the alumina is washed with two liters distilled, deionized water, it is placed under 200 ml of 6 M HCl for 1-2 hours. The alumina is hand-swirled in a 500 ml vacuum flask with distilled, deionized water until clear wash water is seen. The alumina is vacuum washed with three, 200 ml volumes of deionized water. 100 mg of Worthington G.O. is diluted with 100 ml of 0.1 M NaCl and adjusted to pH 4.0 with diluted HCl. Ten mg of succinic acid is added to 50 ml of deionized water and adjusted to pH 4.0 with NaOH, if necessary. One and a half grams of 1-cyclohexyl-3-(2-murpholinethyl)-carbodiimide metho-p-toluene sulfonate (CMC) are added to the succinic acid solution and dissolved. The G.O. solution is added to the wet alumina. The succinic acid/CMC solution is now added to the G.O.-/alumina mixture at a rate of 2 ml/min. After the two volumes are mixed, 1.5 mg CMC in 50 ml of water are added to the mixture of G.O. and alumina at a rate of 0.1 ml/min while the reaction is continued overnight (16-18 hours) at 0-5 degress centigrade, with shaking. At the completion of the reaction the alumina is washed with 2 l of 0.2 M acetate at pH 5.5. The composite may be assayed at once or stored under water of $10^{-7}$ M $PO_4$ at pH 6.5 until used.

EXAMPLE 4

IMMOBILIZED G.O.

30 gm of $-60+70$ mesh (United States Standard Seive) porous alumina having about 0.1 micron diameter pores are sieved through an 80 mesh screen for five minutes. The alumina is washed until clear and then allowed to stand under 200 ml of 6 M HCl for one hour. Sufficient G.O. is dissolved in 30 ml of water to give an absorbance of 1.16 at 450 nm and adjusted to pH 7.5 with 0.1 M HCl or NaOH. Ten mg of succinic anhydride are dissolved in 1 ml of acetone and added to the G.O. solution at a rate of 0.3 ml/10 min. until exhausted. The reaction is allowed to stand for 20 minutes. The alumina is washed with water until clear then suction washed with 200 ml of water. The alumina is added to the G.O. solution and adjusted to pH 4.2, then add 0.1 g of EDC. This solution is allowed to react overnight (16-18 hours) at 0-5 degrees centigrade. During this time, a solution of 0.4 g EDC in 30 ml of water are added at a rate of 0.1 ml/min. Upon completion of the reaction, the composite is washed with 2 l of 0.2 M $(NH_4)_2SO_4$ (enzyme grade-Schwartz Mann), followed by 4 liters of water. The composite may be stored under water of $10^{-7}$ M $PO_4$ at pH 6.5 until used.

EXAMPLE 5

IMMOBILIZED G.O.

Twenty grams of alumina are prepared as in Example 4. One hundred mg of G.O. (from P-L Biochemical Co., G.O. No. 197-7) is dissolved in 50 ml of 0.1 M NaCl. The mixture is centrifuged at about 13,000 g for one-half hour if necessary to clarify, and then adjusted to pH 7.5. To the G.O. solution 23 mg of glutaric anhydride are added and the solution is allowed to stand 40 minutes. The washed alumina is added to the G.O. solution and 1.0 g of CMC is added directly to the solution and the mixture is adjusted to pH 4.0. The reaction is shaken overnight (16-18 hours) at 0-5 degrees centigrade with the addition of 1.5 gm CMC in 40 ml water at the rate of 0.1 ml/min. At completion, the composite is washed with 2 l of 0.2 M acetate, pH 5.5 then stored under water or under $10^{-7}$ M $PO_4$.

EXAMPLE 6

IMMOBILIZED G.O.

Twenty g of alumina are prepared as in example 4. Twenty five ml of G.O. (Miles Labs G.O. Material) are adjusted to pH 4.0 with 0.1 M HCl, as needed. The G.O. solution and 50 ml of 0.1 M NaCl are added simultaneously to the alumina. Add 10 mg of malic acid to 50 ml water and adjust to pH 4.0 with 0.1 M NaOH. Dilute five ml of malic acid solution to 50 ml and add 1.5 g CMC to the diluted malic acid. Add the malic acid/CMC diluted solution to the G.O. solution at a rate of 2 ml/min. The reaction is shaken at 0-5 degrees centigrade for 16-18 hours with the addition of a solution of 1.5 g CMC in 50 ml water at a rate of 0.1 ml/min. After completion the composite may be stored as in Example 5.

EXAMPLE 7

IMMOBILIZATION OF G.O.

Procedure as in Example 4 with the exception of the addition of ten mg of succinic anhydride in acetone to the G.O. solution.

EXAMPLE 8

ACTIVITY ASSAY OF G.O.

G.O. immobilized on porous alumina is assayed by measuring the disappearance of $O_2$ using a YSI Model 53 oxygen monitor. All assays are performed at 20° C. Five ml of 0.01 M acetic buffer is mixed with 0.02 to 0.1 g of immobilized G.O. composite. After a stable baseline is established 0.25 ml of a 1.4 glucose solution is added to start the reaction. After the rate is determined the immobilized enzyme is dried and weighed. The density of the porous alumina is assumed to be 2.6 g/ml. From this procedure the initial activity is determined to be typically between 58 U/ml of alumina and 24 U/ml of alumina, this being on the order of 1-2 mg of deposited enzyme per ml of dry alumina.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for preparing an immobilized composite from a protein having free amino-functional and carboxyl-functional groups, comprising modifying said protein by reacting at least some of said amino-functional groups with a modifying agent selected from a group consisting of: succinic anhydride, succinic acid, malic acid, and glutaric anhydride, to produce a modified protein while leaving some of said amino-functional groups unmodified, depositing said modified protein on the surface of a porous, inorganic support having a high surface area by maintaining said composite within a pH and temperature range which facilitates deposition of said protein, and directly reacting said unmodified groups of said deposited protein with free functional groups in the presence of a carbodiimide agent to form peptide bonds between said deposited proteins, whereby an immobilized protein-support composite is prepared.

2. The method according to claim 1, wherein said support is −60+70 mesh, U.S. Standard Sieve, having about 0.1 micron diameter pores.

3. The method according to claim 1, wherein said support is −60+70 mesh, U.S. Standard Sieve, porous alumina having about 0.1 micron diameter pores.

4. The method according to claim 1, wherein said carbodiimide is 1-ethyl-3(3-dimethylaminopropyl)-carbodiimide HCl.

5. The method according to claim 1, wherein said protein is an enzyme.

6. The method according to claim 1, wherein said protein is glucose oxidase.

7. The method according to claim 1, wherein said inorganic support is alumina.

8. The method according to claim 7, wherein said alumina is activated prior to the deposition of said protein by contact with aqueous hydrochloric acid for a sufficient period of time.

9. The method according to claim 1, wherein said pH range is about 3.5 to about 9.

10. The method according to claim 1, wherein said pH is in the range of about 5 to about 8.

11. The method according to claim 1, wherein said temperature is in the range between 5° and 50° C.

12. The method according to claim 1, wherein said temperature is in the range between 15° and 25° C.

13. The method according to claim 1, wherein said carbodiimide is 1-cyclohexyl-3-(2-murpholinethyl)-carbodiimide metho-p-toluene sulfonate.

14. An immobilized protein composite made in accordance with the method of claim 1.

15. The immobilized composite of claim 14, wherein said protein is an enzyme.

16. The immobilized composite of claim 14, wherein said protein is glucose oxidase.

17. An immobilized composite of claim 14, wherein said support is alumina.

* * * * *